United States Patent [19]

Berka et al.

[11] Patent Number: 5,843,745

[45] Date of Patent: Dec. 1, 1998

[54] PURIFIED SCYTALIDIUM LACCASES AND NUCLEIC ACIDS ENCODING SAME

[75] Inventors: Randy Michael Berka; Sheryl Ann Thompson, both of Davis; Feng Xu, Woodland, all of Calif.

[73] Assignee: Novo Nordisk A/S, Bagsvaerd, Denmark

[21] Appl. No.: 539,134

[22] Filed: Oct. 4, 1995

Related U.S. Application Data

[62] Division of Ser. No. 253,784, Jun. 3, 1994, abandoned.

[51] Int. Cl.$^6$ .............................. C12N 9/02; C12N 1/00
[52] U.S. Cl. ............................................ 435/189; 435/911
[58] Field of Search ............................... 435/189, 254.11, 435/254.3, 913, 917

[56] References Cited

FOREIGN PATENT DOCUMENTS 9105839  5/1991  WIPO .

OTHER PUBLICATIONS

Berka et al., Abstracts of Papers, BIOT 196, vol. 209, No. 1–2, 1995.
Germann et al., The Journal of Biological Chemistry, vol. 263, No. 2, pp. 885–896, 1988.

*Primary Examiner*—Robert A. Wax
*Assistant Examiner*—Elizabeth Slobodyansky
*Attorney, Agent, or Firm*—Steve T. Zelson; Karen A. Lowrey

[57] ABSTRACT

The present invention relates to isolated nucleic acid constructs containing a sequence encoding a Scytalidium laccase, and the laccase proteins encoded thereby.

5 Claims, 12 Drawing Sheets

```
1    CTGAATTTAAATACAGGAAGATCGCATTCAATCCAGCCTAGACTGCACAATGGTTCTGCA                        60

61   CGACCGTCGCACACCTGCCAATAGTGTTAATAACGGCCTAATACC ATG AAG CGC TT                        116
                                                   M   K   R   F

117  C TTC ATT AAT AGC CTT CTG CTT CTC GCA GGG CTC CTC AAC TCA GG                        161
       F   I   N   S   L   L   L   L   A   G   L   L   N   S   G

162  G GCC CTC GCG CCG GCT CCG TCT ACA CAT CCC AGA TCA AAC CCC GAC AT                    206
       A   L   A   P   A   P   S   T   H   P   R   S   N   P   D   I

207  A CTG CTT GAA AGA GAT GAC CAC TCC CTT ACG TCT CGG CAA GGT AG                        251
       L   L   E   R   D   D   H   S   L   T   S   R   Q   G   S

252  C TGT CAT TCT CCA AGC AAC CGC GCC TGT TGG TGC TCT GGC TTC GA                        296
       C   H   S   P   S   N   R   A   C   W   C   S   G   F   D

297  T ATC AAC ACG GAT TAT GAG ACC AAG ACT CCA AAC ACC GGA GTG GT                         341
       I   N   T   D   Y   E   T   K   T   P   N   T   G   V   V

342  G CGG CGG GTTAGTATCCCAAGTTACGTTTGACCAAGAAATGGACGTGAAGTGTGCTG                         398
       R   R

399  ACTCTCCCGCTAG TAC ACC TTT GAT ATC ACC GAA GTC GAC AAC CGC CC                         446
                    Y   T   F   D   I   T   E   V   D   N   R   P
```

Fig. 1A

```
447  C GGT CCC GAT GGG GTC ATC AAG GAG AAG CTC ATG CTT ATC AAC GA     491
       G   P   D   G   V   I   K   E   K   L   M   L   I   N   D

492  C AAA CTC CTG G GTAGGGTCCTCTCGAACGCCTGCGTCTGCCACACAGCGTAAAACT    547
       K   L   L

548  AACGAACCGCTAG GC CCG ACA GTC TTC GCA AAC TGG GGC GAC ACC ATC     595
                     G   P   T   V   F   A   N   W   G   D   T   I

596  GAG GTG ACC GTC AAC CAC CTG AGA ACC AAC GG GTAAGCGTTCGGA          643
      E   V   T   V   N   H   L   R   T   N   G

644  CACAAAGCCCAGCAACCTAGACACACTCAACTGACCAAGTAG A ACC TCC ATC CAC     698
                                                    T   S   I   H

699  TGG CAC GGC TTG CAC CAA AAA GGA ACC AAC TAC CAC GAC GGC GCC     743
      W   H   G   L   H   Q   K   G   T   N   Y   H   D   G   A

744  AAC GGC GTG ACC GAG TGT CCC ATC CCG CCC GGT GGC TCC CGA GTC     788
      N   G   V   T   E   C   P   I   P   P   G   G   S   R   V

789  TAC AGC TTC CGA GCG CGC CAA TAT GGA ACG TCA TGG TAC CAC TCC     833
      Y   S   F   R   A   R   Q   Y   G   T   S   W   Y   H   S
```

Fig. 1B

| | | | | | | | | | | |
|---|---|---|---|---|---|---|---|---|---|---|
| 834 | CAC H | TTC F | TCC S | GCC A | CAG Q | TAT Y | GGC G | AAC N | GGC G | GTG V | AGC S | GGC G | GCC A | ATC I | CAG Q | 878 |
| 879 | ATC I | AAC N | GGA G | CCC P | GCC A | TCC S | CTG L | CCC P | TAC Y | GAC D | ATC I | GAC D | CTC L | GGC G | GTC V | 923 |
| 924 | CTC L | CCG P | CTG L | CAG Q | GAC D | TGG W | TAC Y | TAC Y | AAG K | TCC S | GCC A | GAC D | CAG Q | CTC L | GTC V | 968 |
| 969 | ATC I | GAG E | ACC T | CTG L | GCC A | AAG K | GGC G | AAC N | GCT A | CCG P | TTC F | AGC S | GAC D | AAC N | GTC V | 1013 |
| 1014 | CTC L | ATC I | AAC N | GGC G | ACC T | GCA A | AAG K | CAC H | CCC P | ACC T | ACT T | GGC G | GAA E | GGG G | GAG E | 1058 |
| 1059 | TAC Y | GCC A | ATC I | GTG V | AAG K | CTC L | ACC T | CCG P | GGC G | AAA K | CGC R | CAT H | CGC R | CTG L | CGG R | 1103 |
| 1104 | CTC L | ATC I | AAC N | ATG M | TCG S | GTG V | GAG E | AAC N | CAC H | TTC F | CAG Q | GTC V | TCG S | CTG L | GCG A | 1148 |
| 1149 | AAG K | CAC H | ACC T | ATG M | ACG T | GTC V | ACG T | ATC I | GCG A | GCG A | GAC D | ATG M | GTC V | CCC P | GTC V | AAC N | 1193 |

Fig. 1C

| 1194 | GCC A | ATG M | ACC T | GTC V | GAC D | AGC S | CTG L | TTT F | ATG M | GCC A | GTC V | GGG G | CAG Q | CGG R | TAT Y | 1238 |
| 1239 | GAT D | GTT V | ACC T | ATC I | GAC D | GCG A | AGC S | CAG Q | GCG A | GTG V | GGG G | AAT N | TAC Y | TGG W | TTC F | 1283 |
| 1284 | AAC N | ATC I | ACC T | TTT F | GGA G | GGG G | CAG Q | CAG Q | AAG K | TGC C | GGC G | TTC F | TCG S | CAC H | AAT N | 1328 |
| 1329 | CCG P | GCG A | CCG P | GCA A | GCC A | ATC I | TTT F | CGC R | TAC Y | GAG E | GGC G | GCT A | CCT P | GAC D | GCT A | 1373 |
| 1374 | CTG L | CCG P | ACG T | GAT D | CCT P | GGC G | GCT A | GCG A | CCA P | AAG K | GAT D | CAT H | CAG Q | TGC C | CTG L | 1418 |
| 1419 | GAC D | ACT T | TTG L | GAT D | CTT L | TCA S | CCG P | GTG V | GTG V | CAA Q | AAC N | AAG K | AAC N | GTG V | CCG P | GTT V | 1463 |
| 1464 | GAC D | GGG G | TTC F | GTC V | AAA K | GAG E | CCT P | GGC G | AAT N | ACG T | CTG L | CCG P | GTG V | ACG T | CTC L | 1508 |
| 1509 | CAT H | GTT V | GAC D | CAG Q | GCC A | GCG A | GCT A | CCA P | CAC H | GTG V | TTT F | ACG T | TGG W | AAG K | ATC I | 1553 |

Fig. 1D

```
1554  AAC GGG AGC GCT GCG GAC GTG GAC TGG GAC AGG CCG GTG CTG GAG  1598
       N   G   S   A   A   D   V   D   W   D   R   P   V   L   E

1599  TAT GTC ATG AAC AAT GAC CTG TCT AGC ATT CCG GTC AAG AAC AAC  1643
       Y   V   M   N   N   D   L   S   S   I   P   V   K   N   N

1644  ATT GTG AGG GTG GAC GGA GTC AAC GAG TGG ACG TAC TGG CTC GTC  1688
       I   V   R   V   D   G   V   N   E   W   T   Y   W   L   V

1689  GAA AAC GAC CCG GAG GGC CGC CTC AGT TTG CCG CAT CCG ATG CAT  1733
       E   N   D   P   E   G   R   L   S   L   P   H   P   M   H

1734  CTA CAC GTAAGTCACATCCCCACTACCATTCGGAATGACCACCAGTACTGACACC    1790
       L   H

1791  CTCCTCCTCAATAG GGA CAC GAT TTC TTT GTC CTA GGC CGC.TCC CCC G  1838
                      G   H   D   F   F   V   L   G   R   S   P

1839  AC GTC TCG CCC GAT TCA GAA ACC CGC TTC GTC TTT GAC CCG GCC G  1883
       D   V   S   P   D   S   E   T   R   F   V   F   D   P   A

1884  TC GAC CTC CCC CGT CTG CGC GGA CAC AAC CCC GTC CGG CGC GAC G  1928
       V   D   L   P   R   L   R   G   H   N   P   V   R   R   D
```

Fig. 1E

```
1929  TC ACC ATG CTT CCC GCG CGC GGC TGG CTG CTG GCC TTC CGC A   1973
         T   M   L   P   A   R   G   W   L   L   A   F   R

1974  CG GAC AAC CCG GGC GCG TGG TTC CAC TGC CAC ATC GCG TGG C   2018
         D   N   P   G   A   W   F   H   C   H   I   A   W

2019  AC GTG TCG GGC GGG TTA AGC GTC GAC TTT CTG GAG CGG GAC G   2063
         V   S   G   G   L   S   V   D   F   L   E   R   D

2064  AG CTG CGC GGG CAG CTG ACG GGA GAG AGC AAG GCG GAG TTG E   2108
         L   R   G   Q   L   T   G   E   S   K   A   E   L

2109  GT GTT TGT CGC GGG GAG TGG AAG GAT TGG GAG GCG AAG AGC C   2153
         V   C   R   G   E   W   K   D   W   E   A   K   S

2154  GG AAG ATC GAT TCG GGG TTG AAG CAG CGG CGA TGG GAT GCG G   2198
         K   I   D   S   G   L   K   Q   R   R   W   D   A   *

2199  GTAGTTGGGCGGATTGTTTAACACGTAGTGGGTAAGGTTGGGCGGGTTTGTTTGGCGTT   2258
```

Fig. 1F

2259 TTCAGGGGTTGGGGTGCGGATGCTGGTCATCCGGGAAACGGCTCTACAACTGGTGTCAAT 2318
2319 AGACTAATATAGAGTGATCAAAGAACTGAGGTTCTGAAAGAGGCGTGAAGTCGCGTTGT 2378
2379 GACTCCCCTTTGCCATGTTGGGAAGTGTGGCTCAACATTGTGTTCAGGTTTGCTCAGGGTG 2438
2439 ATNTCGAACTGACGTNTTGATGAGGGTTATTGCNTAGA 2476

Fig. 1G

PURIFIED SCYTALIDIUM LACCASES AND NUCLEIC ACIDS ENCODING SAME

This is a divisional application of application Ser. No. 08/253,784, filed Jun. 3, 1994, abandoned, the contents of which are incorporated herein by reference in their entirety.

FIELD OF THE INVENTION

The present invention relates to isolated nucleic acid fragments encoding a fungal oxidoreductase enzyme and the purified enzymes produced thereby. More particularly, the invention relates to nucleic acid fragments encoding a phenol oxidase, specifically a laccase, of a thermophilic fungus, Scytalidium.

BACKGROUND OF THE INVENTION

Laccases (benzenediol:oxygen oxidoreductases) are multi-copper containing enzymes that catalyze the oxidation of phenolics. Laccase-mediated oxidations result in the production of aryloxy-radical intermediates from suitable phenolic substrate; the ultimate coupling of the intermediates so produced provides a combination of dimeric, oligomeric, and polymeric reaction products. Such reactions are important in nature in biosynthetic pathways which lead to the formation of melanin, alkaloids, toxins, lignins, and humic acids. Laccases are produced by a wide variety of fungi, including ascomycetes such as Aspergillus, Neurospora, and Podospora, the deuteromycete Botrytis, and basidiomycetes such as Collybia, Fomes, Lentinus, Pleurotus, Trametes, and perfect forms of Rhizoctonia. Laccase exhibits a wide range of substrate specificity, and each different fungal laccase usually differs only quantitatively from others in its ability to oxidize phenolic substrates. Because of the substrate diversity, laccases generally have found many potential industrial applications. Among these are lignin modification, paper strengthening, dye transfer inhibition in detergents, phenol polymerization, juice manufacture, phenol resin production, and waste water treatment.

Although the catalytic capabilities are similar, laccases made by different fungal species do have different temperature and pH optima, and these may also differ depending on the specific substrate. A number of these fungal laccases have been isolated, and the genes for several of these have been cloned. For example, Choi et al. (Mol. Plant-Microbe Interactions 5: 119–128, 1992) describe the molecular characterization and cloning of the gene encoding the laccase of the chestnut blight fungus, *Cryphonectria parasitica*. Kojima et al. (J. Biol. Chem. 265: 15224–15230, 1990; JP 2-238885) provide a description of two allelic forms of the laccase of the white-rot basidiomycete *Coriolus hirsutus*. Germann and Lerch (Experientia 41: 801,1985; PNAS USA 83: 8854–8858, 1986) have reported the cloning and partial sequencing of the *Neurospora crassa* laccase gene. Salohe- imo et al. (J. Gen. Microbiol. 137: 1537–1544, 1985; WO 92/01046) have disclosed a structural analysis of the laccase gene from the fungus *Phlebia radiata*.

Attempts to express laccase genes in heterologous fungal systems frequently give very low yields (Kojima et al., supra; Saloheimo et al., Bio/Technol. 9: 987–990, 1991). For example, heterologous expression of *Phlebia radiata* laccase in *Trichoderma reesei* gave only 20 mg per liter of active enzyme (Saloheimo, 1991, supra). Although laccases have great commercial potential, the ability to express the enzyme in significant quantities is critical to their commercial utility. At the present time there are no laccases which are expressed at high levels in commercially utilized hosts such as Aspergillus. Thus, the need exists for a laccase which can be produced in commercially useful (i.e., gram per liter or more) quantities. The present invention fulfills such a need.

SUMMARY OF THE INVENTION

The present invention relates to a DNA construct containing a nucleic acid sequence encoding a Scytalidium laccase. The invention also relates to an isolated laccase encoded by the nucleic acid sequence. Preferably, the laccase is substantially pure. By "substantially pure" is meant a laccase which is essentially (i.e., $\geq 90\%$) free of other non-laccase proteins.

In order to facilitate production of the novel laccase, the invention also provides vectors and host cells comprising the claimed nucleic acid fragment, which vectors and host cells are useful in recombinant production of the laccase. The nucleic acid fragment is operably linked to transcription and translation signals capable of directing expression of the laccase protein in the host cell of choice. A preferred host cell is a fungal cell, most preferably of the genus Aspergillus. Recombinant production of the laccase of the invention is achieved by culturing a host cell transformed or transfected with the nucleic acid fragment of the invention, or progeny thereof, under conditions suitable for expression of the laccase protein, and recovering the laccase protein from the culture.

The laccases of the present invention are useful in a number of industrial processes in which oxidation of phenolics is required. These processes include lignin manipulation, juice manufacture, phenol polymerization and phenol resin production.

BRIEF DESCRIPTION OF THE FIGURES

FIG. 1 illustrates the nucleotide(SEQ ID NO: 1) and amino acid (SEQ ID NO: 2) sequence of *Scytalidium thermophila* laccase. Letters without corresponding amino acids in the nucleotide sequence indicate the position of introns.

DETAILED DESCRIPTION OF THE INVENTION

*Scytalidium thermophilum* is a thermophilic deuteromycete, and a member of the Torula-Humicola complex which are recognized as dominant species in mushroom compost. Other members of the complex include *Humicola grisea Traaen var. thermoidea* Cooney & Emerson, H. insolens Cooney & Emerson, and *Torula thermophila* Cooney & Emerson, the latter of which has been reassigned to *Scytalidium thermophilum* by Austwick (N. Z. J. Agric. Res. 19: 25–33, 1976). Straatsma and Samson (Mycol. Res. 97: 321–328, 1993) have recently determined that both *H.*

*grisea var. thermoides* and *H. insolens* should be considered as examples of the species *Scytalidium thermophilum* as well. *S. indonesiacum* (Hedger et al., Trans. Brit Mycol. Soc. 78: 366–366, 1982) may also be synonymous with *S. thermophilum*. Members of the complex are known to be producers of thermostable cellulase and β-glucosidase enzymes (Rao and Murthy, Ind. J. Biochem. Biophys. 25: 687–694, 1988; Hayashida and Yoshioka, Agric. Biol. Chem. 44: 1721–1728, 1980). However, there have been no previous reports of the production of a laccase by Scytalidium, or any of the noted synonymous species. It has now been determined that not only does Scytalidium produce a laccase, but the gene encoding this laccase can be used to produce large yields of the enzyme in convenient host systems such as Aspergillus.

Figure 3:
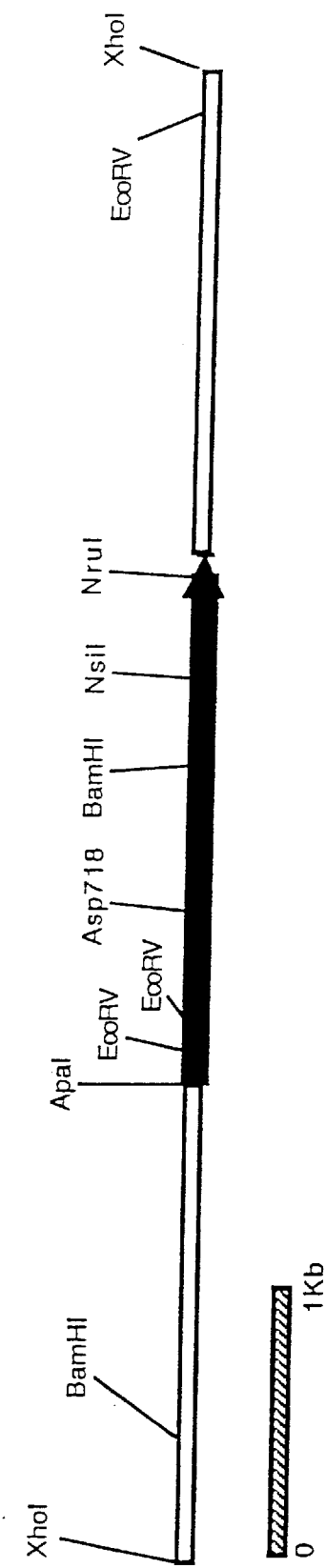
FIG. 3 illustrates the restriction map of a XhoI insert in pShTh6 which contains the *S. thermophilum* laccase (lccS) gene. The approximate position of the lccS coding region is indicated by a solid black line.

To identify the presence of a laccase gene in Scytalidium, a 5' portion of the *Neurospora crassa* laccase gene (lcc1) is used as a probe, under conditions of mild stringency, in southern hybridization of total genomic DNA of different fungal species. An approximately 3 kb laccase specific sequence is detected in the Scytalidium DNA. The *N. crassa* fragment is then used to screen about 12,000 plaques of an *S. thermophilum* genomic DNA library in a λ EMBL4 bacteriophage cloning vector. Nine plaques strongly hybridize with the probe; from these nine, DNA is isolated from four. Each of these clones contains a 3 kb BamHI fragment corresponding to the one initially identified in the southern blot of genomic DNA. One of the fragments is subcloned into a pBluescript vector; however, DNA sequencing shows only a portion of the gene to be on this fragment. A 6 kb fragment XhoI fragment from the same phage contains the whole lccS gene, and this is then subcloned into pBluescript to derive plasmid pShTh6. A restriction map of the 6 kb insert is shown in FIG. 3.

Once the sequence is determined, the positions of introns and exons within the gene is assigned based on alignment of the deduced amino acid sequence to the corresponding *N. crassa* laccase gene product. From this comparison, it appears that the gene (lccS) of *S. thermophilum* is composed of seven exons(243, 91, 70, 1054 and 390 nucleotides) punctuated by four small introns (63, 58, 55 and 65 nucleotides). The coding region, excluding intervening sequences is very GC-rich(60.8% G+C) and encodes a preproenzyme of 616 amino acids: a 21 amino acid signal peptide and a 24 amino acid propeptide. The sequence of the *S. thermophilum* gene and the predicted amino acid sequence is shown in FIG. 1 (SEQ ID NOS: 1 and 2)

The laccase gene is then used to create an expression vector for transformation of Aspergillus host cells. The vector, pShTh15 contains the *A. oryzae* TAKA-amylase promoter and the *A. niger* glaA terminator regions. The construction of pShTh15 is outlined in FIG. 2. Aspergillus cells are cotransformed with the expression vector and a plasmid containing the pyrG or amdS selectable marker. Transformants are selected on the appropriate selective medium containing ABTS. Laccase-producing colonies exhibit a green halo and are readily isolatable. Selected transformants are grown up in shake flasks and culture broths tested for laccase activity by the syringaldazine method. Shake flask cultures are capable of producing 50 or more mg/liter of laccase, and in fermentors, yields of over 1.6 g/liter are observed.

According to the invention, a Scytalidium gene encoding a laccase can be obtained by methods described above, or any alternative methods known in the art, using the information provided herein. The gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene or various activator genes. To permit the secretion of the expressed protein, nucleotides encoding a signal sequence may be inserted prior to the coding sequence of the gene. For expression under the direction of control sequences, a laccase gene to be used according to the invention is operably linked to the control sequences in the proper reading frame. Promoter sequences that can be incorporated into plasmid vectors, and which can direct the transcription of the laccase gene, include but are not limited to the prokaryotic β-lactamase promoter (Villa-Kamaroff, et al., 1978, Proc. Natl. Acad. Sci. U.S.A. 75:3727–3731) and the tac promoter (DeBoer, et al., 1983, Proc. Natl. Acad. Sci. U.S.A. 80:21–25). Further references can also be found in "Useful proteins from recombinant bacteria", in Scientific American, 1980, 242:74–94; and in Sambrook et al., Molecular Cloning, 1989.

The expression vector carrying the DNA construct of the invention may be any vector which may conveniently be subjected to recombinant DNA procedures, and the choice of vector will typically depend on the host cell into which it is to be introduced. Thus, the vector may be an autonomously replicating vector, i.e. a vector which exists as an extrachromosomal entity, the replication of which is independent of chromosomal replication, e.g. a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), or the promoters of the *Bacillus subtilis* xylA and xylB genes. In a yeast host, a useful promoter is the eno-1 promoter. For transcription in a fungal host, examples of useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (glaA), *Rhizomucor miehei* lipase, *A. oryzae* alkaline protease, *A. oryzae* triose phosphate isomerase or *A. nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the laccase of the invention. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis,* or one which confers antibiotic resistance such as ampicillin, kanamycin, chloramphenicol or tetracycline resistance. Examples of Aspergillus selection markers include amdS, pyrG, argB, niad, sC, and hygB a marker giving rise to hygromycin resistance. Preferred for use in an Aspergillus host cell are the amds and pyrg markers of *A. nidulans* or *A. oryzae.* A frequently used mammalian marker is the dihydrofolate reductase (DHFR) gene. Furthermore, selection may be accomplished by co-transformation, e.g. as described in WO 91/17243.

It is generally preferred that the expression gives rise to a product that is extracellular. The laccases of the present invention may thus comprise a preregion permitting secretion of the expressed protein into the culture medium. If desirable, this preregion may be native to the laccase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei,* the gene for the α-factor from *Saccharomyces cerevisiae* or the calf preprochymosin gene. Particularly preferred, when the host is a fungal cell, is the preregion for *A. oryzae* TAKA amylase, *A. niger* neutral amylase, the maltogenic amylase form Bacillus NCIB 11837, *B. stearothermophilus* α-amylase, or *Bacillus licheniformis* subtilisin. An effective signal sequence is the *A. oryzae* TAKA amylase signal, the *Rhizomucor miehei* aspartic proteinase signal and the *Rhizomucor miehei* lipase signal.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. Nolecular Cloning, 1989).

The cell of the invention either comprising a DNA construct or an expression vector of the invention as defined above is advantageously used as a host cell in the recombinant production of a enzyme of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous or heterologous is recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus inegaterium, Bacillus thuringiensis,* or *Streptomyces lividans* or *Streptomyces murinus,* or gram negative bacteria such as *E. coli.* The transformation of the bacteria may for instance be effected by protoplast transformation or by using competent cells in a manner known per se.

The host cell may also be a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces or Schizosaccharomyces, e.g. *Saccharomyces cerevisiae.* Useful filamentous fungi may selected from a species of Aspergillus, e.g. *Aspergillus oryzae* or *Aspergillus niger.* Alternatively, a strain of a *Fusarium species,* e.g. *F. oxysporum,* can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989.

The present invention thus provides a method of producing a recombinant laccase of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the laccase of the invention. Suitable media are available from commercial suppliers or may be prepared according to published formulae (e.g. in catalogues of the American Type Culture Collection).

The resulting enzyme may be recovered from the medium by conventional procedures including separating the cells from the medium by centrifugation or filtration, precipitating the proteinaceous components of the supernatant or filtrate by means of a salt, e.g. ammonium sulphate, followed by purification by a variety of chromatographic procedures, e.g. ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of laccase is achieved in a fungal host cell, such as Aspergillus. As described in detail in the following examples, the laccase gene is ligated into a plasmid containing the *Aspergillus oryzae* TAKA α-amylase promoter, and the *Aspergillus nidulans* amds selectable marker. Alternatively, the amdS may be on a separate plasmid and used in co-transformation. The plasmid (or plasmids) is used to transform an Aspergillus species host cell, such as *A. oxyzae* or *A. niger* in accordance with methods described in Yelton et al. (PNAS USA 81: 1470–1474, 1984).

Those skilled in the art will recognize that the invention is not limited to use of the nucleic acid fragments specifically disclosed herein, for example, in FIG. 1. It will also be apparent that the invention encompasses those nucleotide sequences that encode the same amino acid sequences as depicted in FIG. 1, but which differ from those specifically depicted nucleotide sequences by virtue of the degeneracy of the genetic code. Also, reference to FIG. 1, in the specification and the claims will be understood to encompass both the genomic sequence depicted therein as well as the corresponding CDNA and RNA sequences, and the phrases "DNA construct" and "nucleic acid sequences" as used herein will be understood to encompass all such variations.

"DNA construct" shall generally be understood to mean a DNA molecule, either single- or double-stranded, which may be isolated in partial form from a naturally occurring gene or which has been modified to contain segments of DNA which are combined and juxtaposed in a manner which would not otherwise exist in nature.

In addition, the invention also encompasses other Scytalidium laccases, including alternate forms of laccase which may be found in S. thermophilum and as well as laccases which may be found in other fungi which are synonyms or fall within the definition of Scytalidium thermophilum as defined by Straatsma and Samson, 1993, supra. These include S. indonesiacum, Torula thermophila, Humicola brevis var. thermoidea, Humicola brevispora, H. grisea var. thermoidea, Humicola insolens, and Humicola lanuginosa (also known as Thermomyces lanuginosus). The invention also provides the means for isolation of laccase genes from other species of Scytalidium, such as S. acidophilum, S. album, S. aurantiacum, S. circinatum, S. flaveobrunneum, S. hyalinum, S. lignicola, and S. uredinicolum. Identification and isolation of laccase genes from sources other than those specifically exemplified herein can be achieved by utilization of the methodology described in the present examples, with publicly available Scytalidium strains. Alternately, the sequence disclosed herein can be used to design primers and/or probes useful in isolating laccase genes by standard PCR or southern hybridization techniques, using the same publicly available strains. Examples of such publicly available strains include, from the American Type Culture Collection, ATCC 16463, 28085, 36346, 48409, 66938 (S. thermophilum); 24569 (S. acidophilum); 16675 (S. album); 22477 (S. aurantiacum); 66463 (S. circinatum); 13212 (S. flavobrunneum); 52297 (S. fulvum); 38906 (S. hyalinum); 46858 (S. indonesiacum); 18984 (S. indonesiacum); 32382 (S. uredinaolum); from the International Mycological Institute (IMI; United Kingdom), IMI 243 118 (S. thermophilum); from Centraalbureau voor Schimmelcultures (CBS; Netherlands) CBS 183.81, 671.88 (S. thermophilum) 367.72 (S. acidophilum); 372.65 (S. album); 374.65 (S. aurantiacum); 654.89 (S. circinatum); 244.59 (S. flavo-brunneum); 145.78 (S. hyalinum); 259.81 (S. indonesiacum); 233.57 (S. lignicola); 171.40 (S. terminale); 616.84(S. muscorum); from Deutsche Sammlung von Mikroorganismenn und Zellkulturen (DSM; Germany) DSM 2842 (S thermophilum); DSM 2695 (S. lignicola). The invention also encompasses any variant nucleotide sequence, and the protein encoded thereby, which protein retains at least about an 80%, preferably about 85%, and most preferably at least about 90–95% homology with the amino acid sequence depicted in FIG. 1, and which qualitatively retains the laccase activity of the sequence described herein. Useful variants within the categories defined above include, for example, ones in which conservative amino acid substitutions have been made, which substitutions do not significantly affect the activity of the protein. By conservative substitution is meant that amino acids of the same class may be substituted by any other of that class. For example, the nonpolar aliphatic residues Ala, Val, Leu, and Ile may be interchanged, as may be the basic residues Lys and Arg, or the acidic residues Asp and Glu. Similarly, Ser and Thr are conservative substitutions for each other, as are Asn and Gln. It will be apparent to the skilled artisan that such substitutions can be made outside the regions critical to the function of the molecule and still result in an active enzyme. Retention of the desired activity can readily be determined by conducting a standard ABTS oxidation method, such as is described in the present examples.

The protein can be used in number of different industrial processes. These processes include polymerization of lignin, both Kraft and lignosulfates, in solution, in order to produce a lignin with a higher molecular weight. A neutral/alkaline laccase is a particular advantage in that Kraft lignin is more soluble at higher pHs. Such methods are described in, for example, Jin et al., Holzforschung 45(6): 467–468, 1991; U.S. Pat. No. 4,432,921; EP 0 275 544; PCT/DK93/00217, 1992. Laccase is also useful in the copolymerization of lignin with low molecular weight compounds, such as is described in Appl. Microbiol. Biotechnol. 40: 760–767.

The laccase of the present invention can also be used for in-situ depolymerization of lignin in Kraft pulp, thereby producing a pulp with lower lignin content. This use of laccase is an improvement over the current use of chlorine for depolymerization of lignin, which leads to the production of chlorinated aromatic compounds, which are an environmentally undesirable by-product of paper mills. Such uses are described in, for example, Current opinion in Biotechnology 3: 261–266, 1992; J. Biotechnol. 25: 333–339, 1992; Hiroi et al., Svensk papperstidning 5: 162–166, 1976. Since the environment in a paper mill is typically alkaline, the present laccase is more useful for this purpose than other known laccases, which function best under acidic conditions.

Oxidation of dyes or dye precursors and other chromophoric compounds leads to decolorization of the compounds. Laccase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406; WO 92/18683; EP 0495836; Calvo, Mededelingen van de Faculteit Landbouw-wetenschappen/ Rijiksuniversitet Gent.56: 1565–1567, 1991; Tsujino et al., J. Soc. Chem. 42: 273–282, 1991.

The present laccase can also be used for the polymerization or oxidation of phenolic compounds present in liquids. An example of such utility is the treatment of juices, such as apple juice, so that the laccase will accelerate a precipitation of the phenolic compounds present in the juice, thereby producing a more stable juice. Such applications have been described in Stutz, Fruit processing 7/93, 248–252, 1993; Maier et al., Dt. Lebensmittel-rindschau 86(5): 137–142, 1990; Dietrich et al., Fluss. Obst 57(2): 67–73, 1990.

Laccases such as the Scytalidium laccase are also useful in soil detoxification (Nannipieri et al., J. Environ. Qual. 20: 510–517, 1991; Dec and Bollag, Arch. Environ. Contam. Toxicol. 19: 543–550, 1990).

The invention is further illustrated by the following non-limiting examples.

EXAMPLES

I. Isolation of Scytalidum thermophilum Laccase Gene

A. Materials and Methods
1. DNA Extraction and Hybridization analysis

Total cellular DNA is extracted from fungal cells of Scytalidium thermophila strain E421 grown 24 hours in 25 ml of YEG medium (0.5% yeast extract, 2% glucose) using the following protocol: mycelia are collected by filtration through Miracloth (Calbiochem) and washed once with 25 ml of TE buffer. Excess buffer is drained from the mycelia which are subsequently frozen in liquid nitrogen. Frozen mycelia are ground to a fine powder in an electric coffee grinder, and the powder added to 20 ml of TE buffer and 5 ml of 20% SDS (w/v) in a disposable plastic centrifuge tube. The mixture is gently inverted several times to ensure mixing, and extracted twice with an equal volume of phenol:chloroform:isoamyl alcohol (25:24:1). Sodium acetate (3M solution) is added to give a final concentration of 0.3M and the nucleic acids are precipitated with 2.5 volumes of ice cold ethanol. The tubes are centrifuged at 15,000×g for 30 minutes and the pellet is allowed to air-dry for 30 minutes before resuspending in 0.5 ml of TE buffer. DNase-free ribonuclease A is added to a concentration of 100 µg/ml and the mixture is incubated at 37° C. for 30 minutes. Proteinase K (200 µg/ml) is added and each tube is incubated an additional one hour at 37° C. Finally, each sample is extracted twice with phenol:chloroform:isoamyl alcohol before precipitating the DNA with sodium acetate and ethanol. DNA pellets are dried under vacuum, resuspended in TE buffer, and stored at 4° C.

Total cellular DNA samples are analyzed by Southern hybridization. Approximately 5 µg of DNA is digested with EcoRI and fractionated by size on a 1% agarose gel. The gel is photographed under short wavelength UV and soaked for 15 minutes in 0.5M NaOH, 1.5M NaCl followed by 15 minutes in 1 M Tris-HCl, pH 8, 1.5M NaCl. DNA in the gel is transferred onto Zeta-Probe™ hybridization membrane (BioRad Laboratories) by capillary blotting in 20×SSPE (R. W. Davis et al., Advanced Bacterial Genetics, A Manual for Genetic Engineering. Cold Spring Harbor Press. 1980) Membranes are baked for 2 hours at 80° C. under vacuum and soaked for 2 hours in the following hybridization buffer at 45° C. with gentle agitation: 5×SSPE, 35% formamide (v/v), 0.3% SCS, 200 µg/ml denatured and sheared salmon testes DNA. The laccase-specific probe fragment (approx. 1.5 kb) encoding the 5'-portion of the N. crassa lcc1 gene is amplified from N. crassa genomic DNA using standard PCR conditions (Perkin-Elmer Cetus, Emeryville, Calif.) with the following pair of primers: forward primer, 5' CGAGACT-GATAACTGGCTTGG 3' (SEQ ID NO:3); reverse primer, 5' ACGGCGCATTGTCAGGGAAGT 3' (SEQ ID NO:4). The amplified DNA segment is first cloned into a TA-cloning vector (Invitrogen, Inc., San Diego, Calif.), then purified by agarose gel electrophoresis following digestion with EcoRI. The purified probe fragment is radiolabeled by nick translation with $\alpha[^{32}P]$dCTP(Amersham) and added to the hybridization buffer at an activity of approximately $1 \times 10^6$ cpm per ml of buffer. The mixture is incubated overnight at 45° C. in a shaking water bath. Following incubation, the membranes are washed once in 0.2×SSPE with 0.1% SDS at 45° C. followed by two washes in 0.2×SSPE(no SDS) at the same temperature. The membranes are allowed to dry on paper towels for 15 minutes, then wrapped in Saran Wrap™ and exposed to x-ray film overnight at −70° C. with intensifying screens (Kodak).

2. DNA Libraries and Identification of Laccase Clones

Genomic DNA libraries are constructed in the bacteriophage cloning vector λ-EMBL4 (J. A. Sorge, in Vectors, A Survey of Molecular Cloning Vectors and Their Uses, Rodriguez et al., eds, pp. 43–60, Butterworths, Boston, 1988). Briefly, total cellular DNA is partially digested with Sau3A and size-fractionated on low-melting point agarose gels. DNA fragments migrating between 9 kb and 23 kb are excised and eluted from the gel using β-agarase (New England Biolabs, Beverly Mass.). The eluted DNA fragments are ligated with BamHI-cleaved and dephosphorylated λ-EMBL4 vector arms, and the ligation mixtures are packaged using commercial packaging extracts (Stratagene, Lajolla, Calif.). The packaged DNA libraries are plated and amplified on *Escherichia coli* K802 cells. Approximately 10,000–20,000 plaques from each library are screened by plaque-hybridization with the radiolabeled lcc1 DNA fragment using the conditions described above. Plaques which give hybridization signals with the probe are purified twice on *E. coli* K802 cells, and DNA from the corresponding phage is purified from high titer lysates using a Qiagen Lambda kit (Qiagen, Inc., Chatsworth, Calif.).

3. Analysis of Laccase Genes

Restriction mapping of laccase clones is done using standard methods (Lewin, Genes. 2d ed., Wiley & Sons, 1985, New York). DNA sequencing is done with an Applied Biosystems Model 373A automated DNA Sequencer (Applied Biosystems, Inc., Foster City, Calif.) using the primer walking technique with dye-terminator chemistry (H. Giesecke et al., J. Virol. Methods 38: 47–60, 1992). Oligonucleotide sequencing primers are synthesized on an Applied Biosystems model 394 DNA/RNA Synthesizer.

B. Results and Discussion

1. Identification of Laccase Gene Sequence

Total cellular DNA samples are prepared from the species *Neurospora crassa, Botrytis cinerea,* and Scytalidium. Aliquots of these DNA preparations are digested with BamHI and fractionated by agarose gel electrophoresis. DNA in the gel is blotted to a Zeta-Probe™ membrane filter (BioRad Laboratories, Hercules, Calif.) and probed under conditions of mild stringency with a radiolabeled fragment encoding a portion of the *N. crassa* lcc1 gene, as described above. Laccase-specific sequences are detected in the genomes of *S. thermophilum* and the *N. crassa* control, but not in the *B. cinerea* genomic DNA with this probe.

2. Cloning and Characterization of *Scytalidium thermophila* Laccase (StL) Gene

The *S. thermophilum* laccase gene is isolated using plaque hybridization to screen the genomic DNA library made in λ-EMBL4. The library contains approximately 250,000 independent clones before amplification, and 12,000 plaques are screened by hybridization with a radiolabeled *N. crassa* laccase gene fragment as described above. Nine plaques are identified which hybridize strongly to the probe. DNA is isolated from four of these clones and analyzed by restriction mapping. All four contain a 3 kb BamHI fragment that is originally identified in southern blotting with genomic DNA as described above. This fragment is isolated from one clone and inserted into a pBluescript vector (Stratagene Cloning Systems, La Jolla, Calif.). However, DNA sequence analysis indicates that only a portion of the gene is located on this segment. Consequently, a 6 kb XhoI fragment which contains the entire lccS gene is subcloned into pbluescript to derive the plasmid pShTh6. A restriction map of the 6 kb insert in this plasmid is shown in FIG. 3. The nucleic acid sequence is shown in FIG. 1 and SEQ ID NO:1. The deduced amino acid sequence of StL is obtained on the basis of amino acid sequence homology with *N. crassa* laccase. StL shares approximately 58% amino acid sequence identity with NcL, and this sequence similarity is highest among those amino residues that are involved in the formation of the active site copper center. StL, like NcL appears to be synthesized as a preproenzyme (616 amino acids with a 21 amino acid signal peptide and a propeptide of 24 amino acids). However, since the amino terminal sequence of the mature StL protein is not yet determined, the exact length of the propeptide is not certain. There are five potential sites for N-linked glycosylation in StL. A potential C-terminal processing signal with homology to *N. crassa* laccase also exists in StL (Asp-Ser-Gly-Leu*Lys$_{564}$ (SEQ ID NO:5)) which may result in the proteolytic removal of the last seven amino acids from the primary translation product.

The presence of four small introns (63, 58, 55 and 65 nucleotides) is determined by comparing the open reading frames within the coding region of lccS to the primary structure of NcL. Excluding these intervening sequences, the coding region contains 60.8% G+C. The base composition of lccS reflects a bias for codons ending in G or C.

II. Expression of Scytalidium Laccase in Aspergillus

A. Materials and Methods
1. Bacterial and Fungal Host Strains

*Escherichia coli* JM101 (Messing et al., Nucl. Acids Res. 9:309–321, 1981) is used as a host for construction and routine propagation of laccase expression vectors in this study. Fungal hosts for laccase expression included the *Aspergillus niger* strain Bo-1, as well as a uridine-requiring (pyrG) mutant of the α-amylase-deficient *Aspergillus oryzae* strain HowB104.

2. Plasmids

Plasmid pSHTh5 is a pBluescript(Stratagene Cloning Systems, LaJolla, Calif.) derivative which contains a 6 kb XhoI fragment of *S. thermophilum* DNA encoding StL. Plasmid pToC68(WO 91/17243) contains the *A. oryzae* TAKA-amylase promoter and *A. niger* glaa terminator, and pToC90(WO 91/17243) carries the *A. nidulans* amdS gene.

3. Construction of Laccase Expression Vectors

Figure 2A:
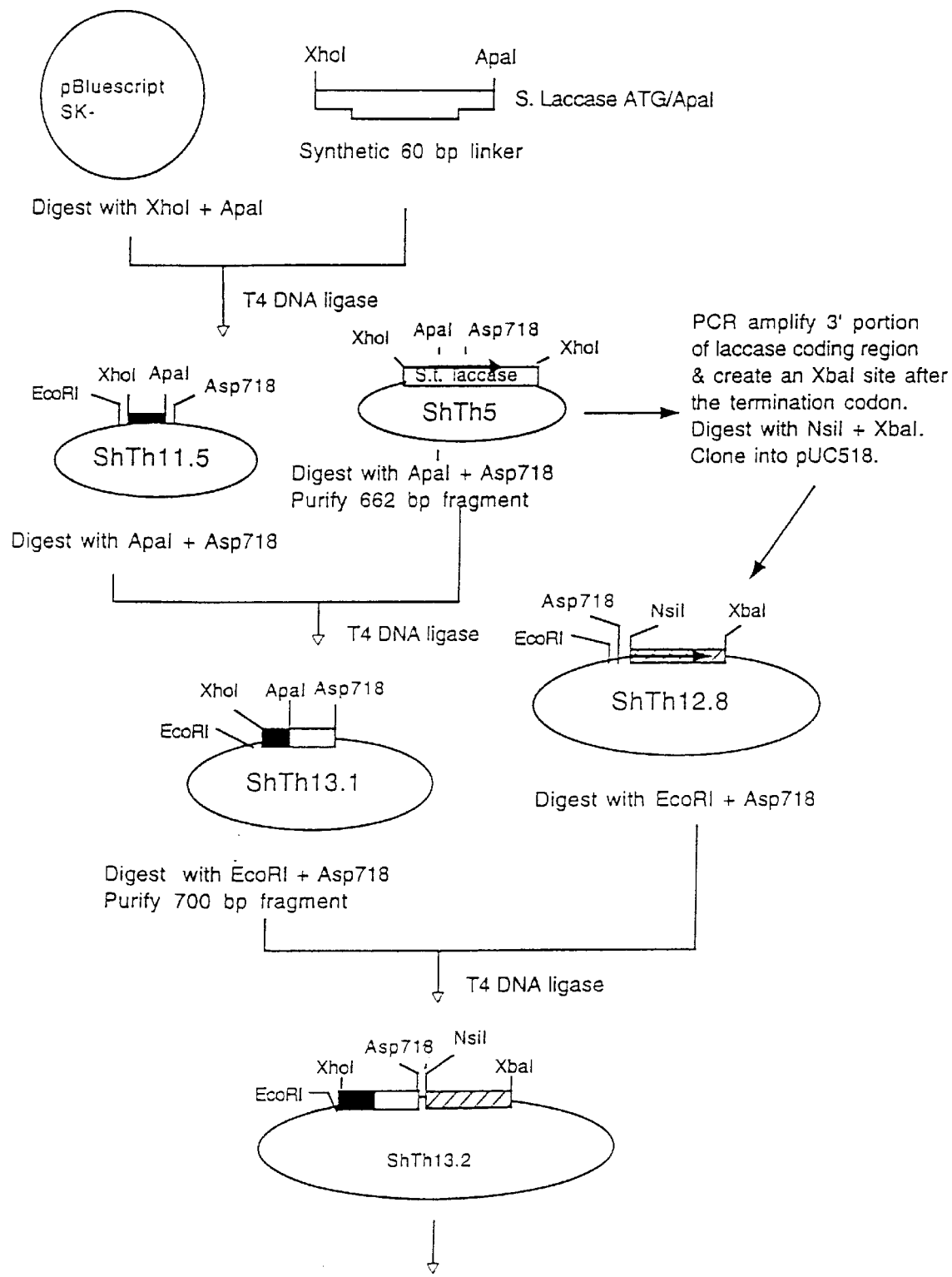
FIG. 2 illustrates the construction of plasmid pShTh15.
Figure 2B:
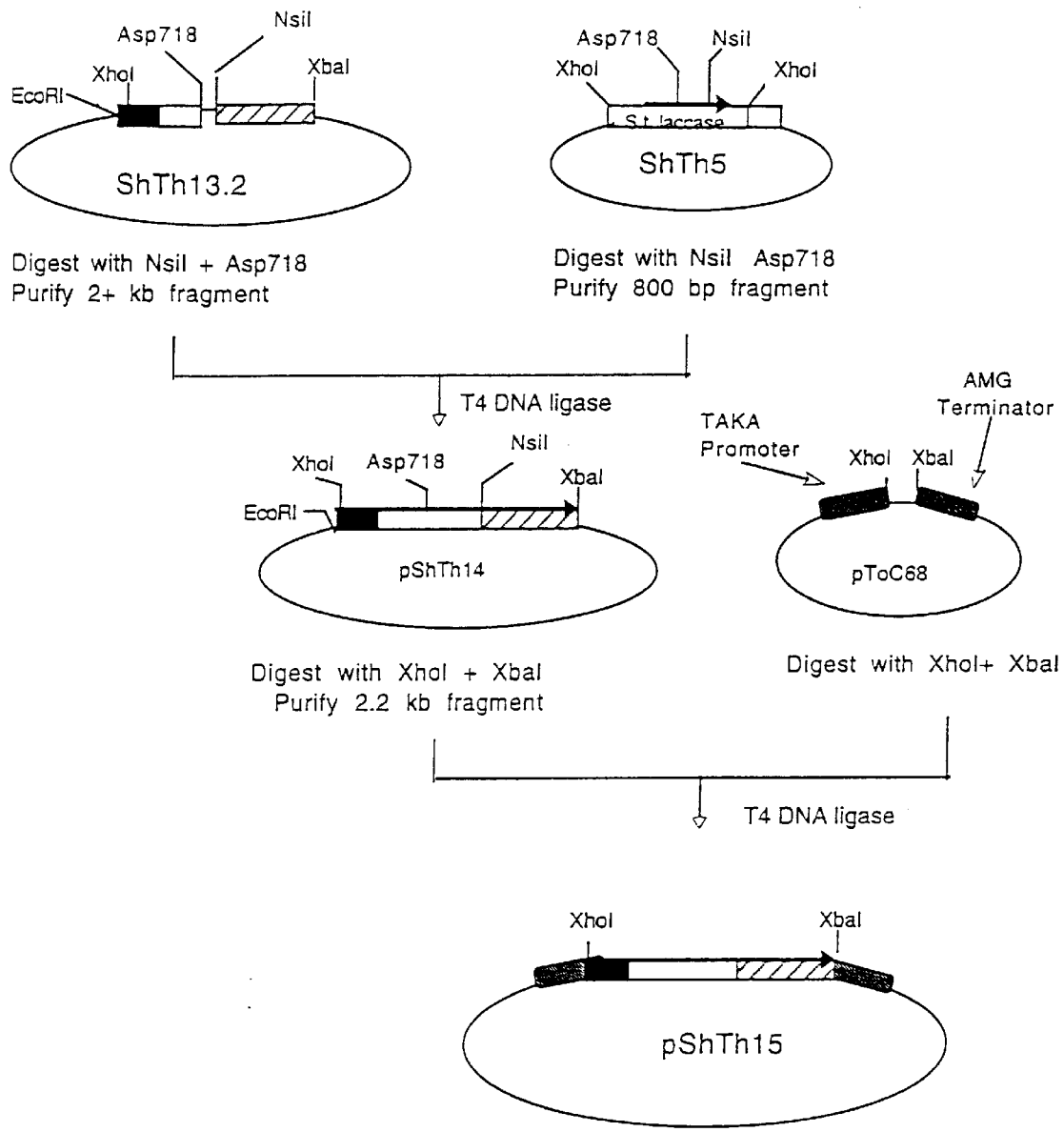

The construction strategy for the laccase expression vector pShTh15 is outlined in FIG. 2. The promoter directing transcription of the laccase gene is obtained from the *A. oryzae* α-amylase (TAKA-amylase) gene (Christensen et al., supra), and terminator from the *A. niger* glaA (glucoamylase) terminator region. The expression vector is constructed as follows. A 60 basepair synthetic DNA linker, 4. Transformation of Aspergillus host cells Methods for co-transformation of Aspergillus strains are as described in Christensen et al., supra. For introduction of the laccase expression vectors into *A. oryzae* HowB 104 pyrG, equal amounts (approximately 5 µg each) of laccase expression vector and pPyrG, which harbors the cloned *A. nidulans* pyrG gene, are used. Protrophic(Pyr$^+$) transformants are selected on Aspergillus minimal medium (Rowlands and Turner, Mol. Gen. Genet. 126: 201–216, 1973), and the transformants are screened for the ability to produce laccase on minimal medium containing 1 mM 2,2'-azinobis(3-ethylbenzthiazolinesulfonic acid) [ABTS]. Cells which secrete active laccase oxidize the ABTS, producing a green halo surrounding the colony. *A. niger* Bo-1 protoplasts are cotransformed using equal amounts (approximately 5 µg each) of laccase expression vector and pToC90 which contains the *A. nidulans* amdS (acetamidase) gene (Hynes et al., Mol. Cell Biol. 3: 1430–1439, 1983. AmdS$^+$ transformants are selected on Cove minimal medium (Cove, Biochim. Biophys. Acta 113: 51–56, 1966) with 1% glucose as the carbon source and acetamide as the sole nitrogen source and screened for laccase expression on Cove medium with 1 mM ABTS.

5. Analysis of Laccase-Producing Transformants

Transformants which produce laccase activity on agar plates are purified twice through conidiospores and spore suspensions in sterile 0.01% Tween-80 are made from each. The density of spores in each suspension is estimated spectrophotometrically ($A_{595}$ nm). Approximately 0.5 absorbance units of spores are used to inoculate 25 ml of ASPO4 or MY50 medium in 125 ml plastic flasks. The cultures are incubated at 37° C. with vigorous aeration (approximately 200 rpm) for four to five days. Culture broths are harvested by centrifugation and the amount of

```
5'   TCGAGATGAAGCGCTTCTTCATTAATAGCCTTCTGCTTCTCGCAGGGCTCCTCAACTCAGGGCC    3'(SEQ ID NO:6)

3'         CTACTTCGCGAAGAAGTAATTATCGGAAGACGAAGAGCGTCCCGAGGAGTTGAGTCC          5'(SEQ ID NO:7)
``` including the region from start codon to an ApaI site, is inserted into XhoI- and ApaI-digested pBluescriptSK- (Stratagene, LaJolla, Calif.) to produce an intermediate termed pShTh11.5. This vector is digested with ApaI and Asp718 and ligated with a 662 base pair ApaI-Asp718 fragment encoding a portion of StL from pShTh5, generating a second intermediate called pShTh13.1. An XbaI site is introduced immediately downstream of the stop codon using pShTh5 as a template for a PCR reaction with the following primers:forward: 5'GTCATGAACAATGACCT 3'(SEQ ID NO:8); reverse: 5'AGAGAGTCTAGATTAAACAATCCGCCCAACTAC3' (SEQ ID NO:9). The amplified fragment is digested with NsiI and XbaI and subcloned into pUC518 to create the intermediate called pShTh12.8. The pShTh12.8 vector is digested with EcoRI and Asp718 and ligated with a 700 base pair EcoRI-Asp718 fragment from pShTh13.1 to generate pShTh13.1 to generate pShTh13.2. An 800 base pair NsiI-Asp718 fragment containing the final portion of the laccase coding region is obtained from pShTh5 and inserted into NsiI- and Asp718-cleaved pShTh13.2 to give pShTh14. Lastly, the 2.2 kb laccase coding region in pShTh14 is removed by cleavage with XhoI and XbaI and inserted between the XhoI and XbaI sites of pToC68 to generate the expression vector pShTh15.

laccase activity in the supernatant is determined using syringaldazine as a substrate. Briefly, 800 µl of assay buffer (25 mM sodium acetate, pH 5.5, 40 µM CuSo$_4$) is mixed with 20 µl of culture supernatant and 60 µl of 0.28 mM syringaldazine stock solution (Sigma Chemical is Co., St. Louis, Mo.) in 50% ethanol. The absorbance at 530 nm is measured over time in a Genesys 5 UV-vis spectrophotometer (Milton-Roy). One laccase unit (LACU) is defined as the amount of enzyme which oxidizes one µmole of substrate per minute at room temperature. SDS-polyacrylamide gel electrophoresis (PAGE) is done using precast 10–27% gradient gels from Novex (San Diego, Calif.). Protein bands are developed using Coomassie Brilliant Blue(Sigma).

B. Results and Discussion
1. Expression of Scytalidium laccase

The expression vector pShTh15 is used in conjunction with pPyrG (*A. nidulans* pyrG) or pToC90(*A. nidulans* amdS) plasmids to generate *A. oryzae* and *A. niger* co-transformants which express StL. The number of laccase-producing co-transformants obtained in *A. oryzae* HowB104pyrG is small (3.7% of Pyr$^+$ transformants) compared to the number obtained in *A. niger* Bo-1 using amdS selection (71.5% of AmdS$^+$ transformants). It is unknown whether this is due to an abnormally low co-transformation (i.e., integration) frequency or extremely low expression or laccase degradation in many *A. oryzae* transformants.

Expression levels of StL range from about 50 mg/l in shake flasks and 1–2 g/l in a fermentor.

III. Purification and Characterization of Recombinant Scytalidum Laccase

A. Materials and Methods

1. Materials

Chemicals used as buffers and substrates are commercial products of at least reagent grade. Chromatography is performed on either a Pharmacia FPLC. Spectroscopic assays are conducted on either a spectrophotometer (Shimadzu PC160) or a microplate reader (Molecular Devices). Britton & Robinson (B&R) buffers are prepared according to the protocol described in Quelle, Biochemisches Taschenbuch, H. M. Raven, II. Teil, S.93 u. 102, 1964.

2. Fermentation

A 1 ml aliquot of a spore suspension of *Aspergillus oryzae* transformant HowB104-pShTh15-2(approximately $10^9$ spores/ml) is added aseptically to a 500 ml shake flask containing 100 ml of sterile shake flask medium (maltose, 50 g/l; $MgSO_4.7H_2O$, 2 g/l; $KH_2PO_4$, 10 g/l; $K_2SO_4$, 2 g/l; $CaCl_2.2H_2O$ 0.5 g/l; Citric acid, 2 g/l; yeast extract, 10 g/l; trace metals [$ZnSO_4.7H_2O$, 14.3 g/l; $CuSO_4.5H_2O$, 2.5 g/l; $NiCl_2.6H_2O$, 0.5 g/l; $FeSO_4.7H_2O$, 13.8 g/l, $MnSO_4.H_2O$, 8.5 g/l; citric acid, 3.0 g/l], 0.5 ml/l; urea, 2 g/l, made with tap water and adjusted to pH 6.0 before autoclaving), and incubated at 37° C. on a rotary shaker at 200 rpm for 18 hours. 50 ml of this culture is aseptically transferred to a 3 liter fermentor containing 1.8 liters of the fermentor media ($MgSO_4.7H_2O$, 2 g/l; $KH_2PO_4$, 2 g/l; citric acid 4 g/l; $K_2SO_4$, 3 g/l; $CaCl_2.2H_2O$, 2 g/l; trace metals, 0.5 ml/l; pluronic antifoam, 1 ml/l). The fermentor temperature is maintained at 34° C. by the circulation of cooling water through the fermentor jacket. Sterile air is sparged through the fermentor at a rate of 1.8 liter/min (1 v/v/m). The agitation rate is maintained between 600 and 1300 rpm at approximately the minimum level required to maintain the dissolved oxygen level in the culture above 20%. Sterile feed (Nutriose 725[maltose syrup], 225 g/l; urea, 30 g/l; yeast extract, 15 g/l; pluronic antifoam, 1.5 ml/l, made up with distilled water and autoclaved) is added to the fermentor by use of a peristaltic pump. The feed rate profile during the fermentation is as follows: 30 g of feed is added initially before inoculation; 0–24 h, 2 g/l h; 24–48 h, 4 g/l h; 48 h-end, 6 g/l.

Copper(in the form of $CuCl_2$, $CuSO4$ or other soluble salt) is made as a 400× stock in water or a suitable buffer, filter sterilized and added aseptically to the tank to a final level of 0.5 mM.

Samples for enzyme activity determination are withdrawn and filtered through Miracloth to remove mycelia. These samples are assayed for laccase activity by the LACU assay described above. Laccase activity is found to increase continuously during the course of the fermentation, with a value of approximately 3.6 LACU/ml achieved after 115 hours in the fermentation containing excess copper. At a specific activity of 1.9 LACU/mg, this corresponds to over 1.8 g/l recombinant laccase expressed by this transformant.

3. Enzymatic Assay

Laccase activity is determined by syringaldazine oxidation at 30° C. in a 1-cm quartz cuvette. 60 $\mu$l syringaldazine stock solution (0.28 mM in 50% ethanol) and 20 gl sample are mixed with 0.8 ml preheated buffer solution. The oxidation is monitored at 530 nm over 5 minutes. The activity is expressed as pnole substrate oxidized per minute. B&R buffers with various pHs are used. The activity unit is referred to here as "SOU". A buffer of 25 mM sodium acetate, 40 $\mu$M $CuSO_4$, pH 5.5, is also used to determine the activity, which is referred to as LACU, as defined above. 2,2'-azinobis(3-ethylbenzo thiazoline-6-sulfonic acid) (ABTS) oxidation assays are done using 0.4 mM ABTS, B&R buffer, pH 4.1, at room temperature by monitoring $\Delta A_{405}$. An ABTS oxidase activity overlay assay is performed by pouring cooled ABTS-agarose(0.05 g ABTS, 1 g agarose, 50 ml $H_2O$, heated to dissolve agarose) over a native-IEF gel and incubating at room temperature. Thermostability analysis is performed using samples that have ~3 $\mu$M enzyme preincubated for one hour in B&R buffer, at pH 2.7, 6.1, and 9.0, and various temperatures. Samples are assayed after a 44-fold dilution into B & R buffer, pH 4.1, at room temperature.

3. Purification from a fermentor broth 1.2 liters of cheese-cloth filtered broth (pH 7.9, 13 mS) is filtered through Whatman #2 filter paper and concentrated on a Spiral Concentrator (Amicon) with a S1Y100 membrane (MWCO:100) to 200 ml. The concentrate is adjusted to 0.86 mS by diluting it in water and reconcentrated on S1Y100 to 324 ml. The washed and concentrated broth has a dense greenish color.

The broth is frozen overnight at −°20° C., thawed the next day(without any loss of activity) and loaded onto a Q-Sepharose XK26 column (120 ml), preequilibrated with 10 mM Tris, pH 7.7, 0.9 mS. The blue laccase band is eluted during a linear gradient with 2M NaCl.

Pooled laccase fractions(44 ml), dialyzed in 3.5 liters of 10 mM NaAc, pH 5.5, 0.8 mS at 4° C. overnight, are loaded onto a Mono-Q 16/10 (40 ml), preequilibrated with 10 mM MES, pH 5.3, 0.8 mS. The laccase eluted during a linear gradient with 1M NaCl shows apparent homogeneity on SDS-PAGE.

4. Analysis of amino acid content and N-terminus

N-terminal sequencing is performed on an ABI 476A sequencer; and total amino acid analysis, from which the extinction coefficient of laccase is determined, is performed on a HP AminoQuant instrument.

B. Results and Discussion

1. Purification

From 1200 ml fermentor broth, about 0.6 g of laccase are isolated. Initial concentration using a membrane with MWCO of 100 kDa removes significant amounts of brown material and small contaminant proteins. The low affinity of the laccase toward Q-Sepharose matrix equilibrated with 10 mM Tris, pH 7.7, facilitates its separation from other impurities. The enriched fractions are further purified by Mono-Q at pH 5.3. Although it has a pI of 5.1, the laccase migrates slowly on Mono-Q and is separated from impurities during the washing by 10 mM MES, pH 5.3. An overall 15-fold purification and a recovery of 60% are achieved.

2. Characterization

The purified laccase shows a MW of 75–80 kDa on SDS-PAGE. The difference between the MW derived from DNA sequence(63 kDa) and the observed MW is attributable to glycosylation. Native IEF shows 3 bands near pI of about 5.1, which are active in ABTS overlay assay.

3. N-terminal Sequencing

Directly sequencing the N-terminus of the purified laccase from samples either in desalted solution or on PVDF membrane are unsuccessful. This result suggests a blocked N-terminus, likely a pyroglutamate site based on the gene sequence.

The spectrum of the blue laccase has absorption maxima at 276 and 602 nm; with $AbS_{280}/AbS_{600}=23$ and $AbS_{330}/AbS_{589}=2.1$. The extinction coefficient determined by amino acid analysis is 1.9 l/(g*cm).

The activity is tested by using either syringaldazine or ABTS as substrates. Expressed as per $AbS_{280}$ or per mg, the laccase has a value of 2.2 or 4.2 units for SOU at pH 7, respectively.

Figure 4:
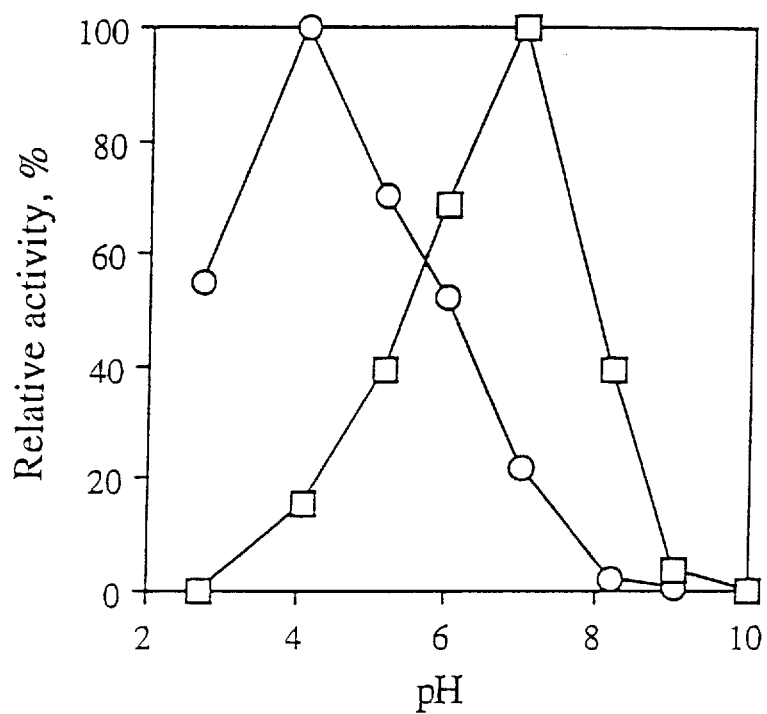
FIG. 4 illustrates the pH profiles of the laccase activity with syringaldazine(squares) and 2,2"azinobis(3-ethylbenzothiazoline-6-sulfonic acid)(circles) as substrate.
Figure 5:
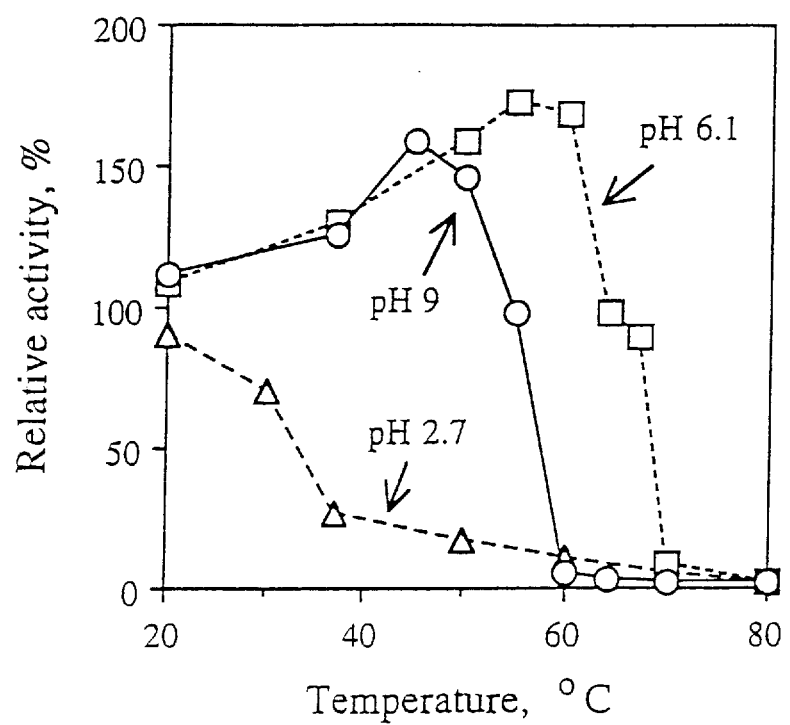
FIG. 5 illustrates the thermostability in B&R buffers of the laccase at pH 2.7, 6.1, and 9.0. Preincubation times are 1 hour. Activities are assayed by ABTS oxidation at 20° C. in B&R buffer, pH 4.1.

The pH profiles of laccase activity has optimal pH of 7 and 4, for syringaldazine and ABTS oxidation, respectively (FIG. 4). Thermostability analysis at three pHs is shown in FIG. 5. The laccase is more stable at neutral to alkaline pH than at acidic pH. Thermoactivation is also observed in neutral-alkaline pH range.

Deposit of Biological Materials

The following biological material has been deposited under the terms of the Budapest Treaty with the Agricultural Research Service Patent Culture Collection, Northern Regional Research Center, 1815 University Street, Peoria, Ill., 61604 and given the following accession number.

| Deposit | Accession Number |
| --- | --- |
| *E. coli* JM101 containing pShTh15 | NRRL B-21262 |

What we claim is:

1. A purified laccase obtained from a Scytalidium strain or strains which have been defined to be equivalent to Scytalidium.

2. A purified laccase obtained from a Scytalidium strain.

3. The laccase of claim 1, which is obtained from *Scytalidium thermophilum* or strains which have been defined to be equivalent to *Scytalidium thermophilum*.

4. The laccase of claim 3, which is obtained from *Scytalidium thernophilum*.

5. A purified laccase which has the amino acid sequence of SEQ ID NO:2 or which is encoded by the nucleic acid sequence contained in plasmid pShTh15 which is contained in *Escherichia coli* NRRL B-21262.

* * * * *

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 2476 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Scytalidium thermophilum ( i x ) FEATURE:
        ( A ) NAME/KEY: intron
        ( B ) LOCATION: 349..411

( i x ) FEATURE:
        ( A ) NAME/KEY: intron
        ( B ) LOCATION: 502..559

( i x ) FEATURE:
        ( A ) NAME/KEY: intron
        ( B ) LOCATION: 632..686

( i x ) FEATURE:
        ( A ) NAME/KEY: intron
        ( B ) LOCATION: 1739..1804

( i x ) FEATURE:
        ( A ) NAME/KEY: CDS
        ( B ) LOCATION: join (106..348, 412..501, 560..631, 687..1738, 1805..2194)

( x i ) SEQUENCE DESCRIPTION: SEQ ID NO: 1:

```
CTGAATTTAA  ATACAGGAAG  ATCGCATTCA  ATCCAGCCTA  GACTGCACAA  TGGTTCTGCA                    60

CGACCGTCGC  ACACCTGCCA  ATAGTGTTAA  TAACGGCCTA  ATACC ATG AAG CGC TTC                    117
                                                    Met Lys Arg Phe
                                                      1

TTC ATT AAT AGC CTT CTG CTT CTC GCA GGG CTC CTC AAC TCA GGG GCC                         165
Phe Ile Asn Ser Leu Leu Leu Leu Ala Gly Leu Leu Asn Ser Gly Ala
  5             10                    15                     20

CTC GCG GCT CCG TCT ACA CAT CCC AGA TCA AAC CCC GAC ATA CTG CTT                         213
Leu Ala Ala Pro Ser Thr His Pro Arg Ser Asn Pro Asp Ile Leu Leu
              25                  30                  35

GAA AGA GAT GAC CAC TCC CTT ACG TCT CGG CAA GGT AGC TGT CAT TCT                         261
Glu Arg Asp Asp His Ser Leu Thr Ser Arg Gln Gly Ser Cys His Ser
          40                  45                  50
```

| | | | | | | | | | | | | | | | | |
|---|---|---|---|---|---|---|---|---|---|---|---|---|---|---|---|---|
| CCA | AGC | AAC | CGC | GCC | TGT | TGG | TGC | TCT | GGC | TTC | GAT | ATC | AAC | ACG | GAT | 309 |
| Pro | Ser | Asn | Arg | Ala | Cys | Trp | Cys | Ser | Gly | Phe | Asp | Ile | Asn | Thr | Asp | |
| | 55 | | | | 60 | | | | | | | 65 | | | | |
| TAT | GAG | ACC | AAG | ACT | CCA | AAC | ACC | GGA | GTG | GTG | CGG | CGG | GTTAGTATCC | | | 358 |
| Tyr | Glu | Thr | Lys | Thr | Pro | Asn | Thr | Gly | Val | Val | Arg | Arg | | | | |
| | 70 | | | | | 75 | | | | | 80 | | | | | |

CAAGTTACGT TGACCAAGA AATGGACGTG AAGTGTGCTG ACTCTCCCGC TAG    411

| | | | | | | | | | | | | | | | | |
|---|---|---|---|---|---|---|---|---|---|---|---|---|---|---|---|---|
| TAC | ACC | TTT | GAT | ATC | ACC | GAA | GTC | GAC | AAC | CGC | CCC | GGT | CCC | GAT | GGG | 459 |
| Tyr | Thr | Phe | Asp | Ile | Thr | Glu | Val | Asp | Asn | Arg | Pro | Gly | Pro | Asp | Gly | |
| | | | 85 | | | | | 90 | | | | | | 95 | | |
| GTC | ATC | AAG | GAG | AAG | CTC | ATG | CTT | ATC | AAC | GAC | AAA | CTC | CTG | GTAGG | | 506 |
| Val | Ile | Lys | Glu | Lys | Leu | Met | Leu | Ile | Asn | Asp | Lys | Leu | Leu | | | |
| | | 100 | | | | | 105 | | | | | | 110 | | | |

GTCCTCTCGA ACGCCTGCGT CTGCCACACA GCGTAAAACT AACGAACCGC TAG    559

| | | | | | | | | | | | | | | | | |
|---|---|---|---|---|---|---|---|---|---|---|---|---|---|---|---|---|
| GGC | CCG | ACA | GTC | TTC | GCA | AAC | TGG | GGC | GAC | ACC | ATC | GAG | GTG | ACC | GTC | 607 |
| Gly | Pro | Thr | Val | Phe | Ala | Asn | Trp | Gly | Asp | Thr | Ile | Glu | Val | Thr | Val | |
| | | | | 115 | | | | | 120 | | | | | 125 | | |
| AAC | AAC | CAC | CTG | AGA | ACC | AAC | GGA | GTAAGCGTTC | | GGACACAAAG | | CCCAGCAACC | | | | 661 |
| Asn | Asn | His | Leu | Arg | Thr | Asn | Gly | | | | | | | | | |
| | | 130 | | | | | 135 | | | | | | | | | |

| | | | | | | | | | | | | | | | | |
|---|---|---|---|---|---|---|---|---|---|---|---|---|---|---|---|---|
| TAGACACACT | | CAACTGACCA | | AGTAG | ACC | TCC | ATC | CAC | TGG | CAC | GGC | TTG | CAC | CAA | | 716 |
| | | | | | Thr | Ser | Ile | His | Trp | His | Gly | Leu | His | Gln | | |
| | | | | | | | | 140 | | | | | | 145 | | |
| AAA | GGA | ACC | AAC | TAC | CAC | GAC | GGC | GCC | AAC | GGC | GTG | ACC | GAG | TGT | CCC | 764 |
| Lys | Gly | Thr | Asn | Tyr | His | Asp | Gly | Ala | Asn | Gly | Val | Thr | Glu | Cys | Pro | |
| | | | | 150 | | | | | 155 | | | | | 160 | | |
| ATC | CCG | CCC | GGT | GGC | TCC | CGA | GTC | TAC | AGC | TTC | CGA | GCG | CGC | CAA | TAT | 812 |
| Ile | Pro | Pro | Gly | Gly | Ser | Arg | Val | Tyr | Ser | Phe | Arg | Ala | Arg | Gln | Tyr | |
| | | | 165 | | | | | 170 | | | | | 175 | | | |
| GGA | ACG | TCA | TGG | TAC | CAC | TCC | CAC | TTC | TCC | GCC | CAG | TAT | GGC | AAC | GGC | 860 |
| Gly | Thr | Ser | Trp | Tyr | His | Ser | His | Phe | Ser | Ala | Gln | Tyr | Gly | Asn | Gly | |
| | | 180 | | | | | 185 | | | | | 190 | | | | |
| GTG | AGC | GGC | GCC | ATC | CAG | ATC | AAC | GGA | CCC | GCC | TCC | CTG | CCC | TAC | GAC | 908 |
| Val | Ser | Gly | Ala | Ile | Gln | Ile | Asn | Gly | Pro | Ala | Ser | Leu | Pro | Tyr | Asp | |
| | 195 | | | | | 200 | | | | | 205 | | | | | |
| ATC | GAC | CTC | GGC | GTC | CTC | CCG | CTG | CAG | GAC | TGG | TAC | TAC | AAG | TCC | GCC | 956 |
| Ile | Asp | Leu | Gly | Val | Leu | Pro | Leu | Gln | Asp | Trp | Tyr | Tyr | Lys | Ser | Ala | |
| 210 | | | | 215 | | | | | 220 | | | | | 225 | | |
| GAC | CAG | CTC | GTC | ATC | GAG | ACC | CTG | GCC | AAG | GGC | AAC | GCT | CCG | TTC | AGC | 1004 |
| Asp | Gln | Leu | Val | Ile | Glu | Thr | Leu | Ala | Lys | Gly | Asn | Ala | Pro | Phe | Ser | |
| | | | | 230 | | | | | 235 | | | | | 240 | | |
| GAC | AAC | GTC | CTC | ATC | AAC | GGC | ACC | GCA | AAG | CAC | CCC | ACC | ACT | GGC | GAA | 1052 |
| Asp | Asn | Val | Leu | Ile | Asn | Gly | Thr | Ala | Lys | His | Pro | Thr | Thr | Gly | Glu | |
| | | | 245 | | | | | 250 | | | | | 255 | | | |
| GGG | GAG | TAC | GCC | ATC | GTG | AAG | CTC | ACC | CCG | GGC | AAA | CGC | CAT | CGC | CTG | 1100 |
| Gly | Glu | Tyr | Ala | Ile | Val | Lys | Leu | Thr | Pro | Gly | Lys | Arg | His | Arg | Leu | |
| | | 260 | | | | | 265 | | | | | 270 | | | | |
| CGG | CTC | ATC | AAC | ATG | TCG | GTG | GAG | AAC | CAC | TTC | CAG | GTC | TCG | CTG | GCG | 1148 |
| Arg | Leu | Ile | Asn | Met | Ser | Val | Glu | Asn | His | Phe | Gln | Val | Ser | Leu | Ala | |
| | 275 | | | | | 280 | | | | | 285 | | | | | |
| AAG | CAC | ACC | ATG | ACG | GTC | ATC | GCG | GCG | GAC | ATG | GTC | CCC | GTC | AAC | GCC | 1196 |
| Lys | His | Thr | Met | Thr | Val | Ile | Ala | Ala | Asp | Met | Val | Pro | Val | Asn | Ala | |
| 290 | | | | | 295 | | | | | 300 | | | | | 305 | |
| ATG | ACC | GTC | GAC | AGC | CTG | TTT | ATG | GCC | GTC | GGG | CAG | CGG | TAT | GAT | GTT | 1244 |
| Met | Thr | Val | Asp | Ser | Leu | Phe | Met | Ala | Val | Gly | Gln | Arg | Tyr | Asp | Val | |
| | | | | 310 | | | | | 315 | | | | | 320 | | |
| ACC | ATC | GAC | GCG | AGC | CAG | GCG | GTG | GGG | AAT | TAC | TGG | TTC | AAC | ATC | ACC | 1292 |
| Thr | Ile | Asp | Ala | Ser | Gln | Ala | Val | Gly | Asn | Tyr | Trp | Phe | Asn | Ile | Thr | |
| | | | 325 | | | | | 330 | | | | | 335 | | | |

| | | | | | | | | | | | | | | | | |
|---|---|---|---|---|---|---|---|---|---|---|---|---|---|---|---|---|
| TTT | GGA | GGG | CAG | CAG | AAG | TGC | GGC | TTC | TCG | CAC | AAT | CCG | GCG | CCG | GCA | 1340 |
| Phe | Gly | Gly | Gln | Gln | Lys | Cys | Gly | Phe | Ser | His | Asn | Pro | Ala | Pro | Ala | |
| | | 340 | | | | 345 | | | | | 350 | | | | | |
| GCC | ATC | TTT | CGC | TAC | GAG | GGC | GCT | CCT | GAC | GCT | CTG | CCG | ACG | GAT | CCT | 1388 |
| Ala | Ile | Phe | Arg | Tyr | Glu | Gly | Ala | Pro | Asp | Ala | Leu | Pro | Thr | Asp | Pro | |
| | 355 | | | | 360 | | | | | 365 | | | | | | |
| GGC | GCT | GCG | CCA | AAG | GAT | CAT | CAG | TGC | CTG | GAC | ACT | TTG | GAT | CTT | TCA | 1436 |
| Gly | Ala | Ala | Pro | Lys | Asp | His | Gln | Cys | Leu | Asp | Thr | Leu | Asp | Leu | Ser | |
| 370 | | | | | 375 | | | | 380 | | | | | | 385 | |
| CCG | GTG | GTG | CAA | AAG | AAC | GTG | CCG | GTT | GAC | GGG | TTC | GTC | AAA | GAG | CCT | 1484 |
| Pro | Val | Val | Gln | Lys | Asn | Val | Pro | Val | Asp | Gly | Phe | Val | Lys | Glu | Pro | |
| | | | | 390 | | | | | 395 | | | | | 400 | | |
| GGC | AAT | ACG | CTG | CCG | GTG | ACG | CTC | CAT | GTT | GAC | CAG | GCC | GCG | GCT | CCA | 1532 |
| Gly | Asn | Thr | Leu | Pro | Val | Thr | Leu | His | Val | Asp | Gln | Ala | Ala | Ala | Pro | |
| | | | 405 | | | | 410 | | | | | 415 | | | | |
| CAC | GTG | TTT | ACG | TGG | AAG | ATC | AAC | GGG | AGC | GCT | GCG | GAC | GTG | GAC | TGG | 1580 |
| His | Val | Phe | Thr | Trp | Lys | Ile | Asn | Gly | Ser | Ala | Ala | Asp | Val | Asp | Trp | |
| | | 420 | | | | | 425 | | | | | 430 | | | | |
| GAC | AGG | CCG | GTG | CTG | GAG | TAT | GTC | ATG | AAC | AAT | GAC | CTG | TCT | AGC | ATT | 1628 |
| Asp | Arg | Pro | Val | Leu | Glu | Tyr | Val | Met | Asn | Asn | Asp | Leu | Ser | Ser | Ile | |
| | 435 | | | | | 440 | | | | | 445 | | | | | |
| CCG | GTC | AAG | AAC | AAC | ATT | GTG | AGG | GTG | GAC | GGA | GTC | AAC | GAG | TGG | ACG | 1676 |
| Pro | Val | Lys | Asn | Asn | Ile | Val | Arg | Val | Asp | Gly | Val | Asn | Glu | Trp | Thr | |
| 450 | | | | | 455 | | | | | 460 | | | | | 465 | |
| TAC | TGG | CTC | GTC | GAA | AAC | GAC | CCG | GAG | GGC | CGC | CTC | AGT | TTG | CCG | CAT | 1724 |
| Tyr | Trp | Leu | Val | Glu | Asn | Asp | Pro | Glu | Gly | Arg | Leu | Ser | Leu | Pro | His | |
| | | | | 470 | | | | | 475 | | | | | | 470 | |
| CCG | ATG | CAT | CTA | CAC | GTAAGTCACA | TCCCCCACTA | CCATTCGGAA | TGACCACCAG | | | | | | | | 1779 |
| Pro | Met | His | Leu | His | | | | | | | | | | | | |
| | | | | 475 | | | | | | | | | | | | |
| GTACTGACAC | CCTCCTCCTC | AATAG | GGA | CAC | GAT | TTC | TTT | GTC | CTA | GGC | CGC | | | | | 1831 |
| | | | Gly | His | Asp | Phe | Phe | Val | Leu | Gly | Arg | | | | | |
| | | | | | | 480 | | | | | 485 | | | | | |
| TCC | CCC | GAC | GTC | TCG | CCC | GAT | TCA | GAA | ACC | CGC | TTC | GTC | TTT | GAC | CCG | 1879 |
| Ser | Pro | Asp | Val | Ser | Pro | Asp | Ser | Glu | Thr | Arg | Phe | Val | Phe | Asp | Pro | |
| | | | | 490 | | | | | 495 | | | | | 500 | | |
| GCC | GTC | GAC | CTC | CCC | CGT | CTG | CGC | GGA | CAC | AAC | CCC | GTC | CGG | CGC | GAC | 1927 |
| Ala | Val | Asp | Leu | Pro | Arg | Leu | Arg | Gly | His | Asn | Pro | Val | Arg | Arg | Asp | |
| | | | 505 | | | | | 510 | | | | | 515 | | | |
| GTC | ACC | ATG | CTT | CCC | GCG | CGC | GGC | TGG | CTG | CTG | CTG | GCC | TTC | CGC | ACG | 1975 |
| Val | Thr | Met | Leu | Pro | Ala | Arg | Glu | Trp | Leu | Leu | Leu | Ala | Phe | Arg | Thr | |
| | | 520 | | | | | 525 | | | | | 530 | | | | |
| GAC | AAC | CCG | GGC | GCG | TGG | TTG | TTC | CAC | TGC | CAC | ATC | GCG | TGR | CAC | GTG | 2023 |
| Asp | Asn | Pro | Gly | Ala | Trp | Leu | Phe | His | Cys | His | Ile | Ala | Trp | His | Val | |
| | 535 | | | | | 540 | | | | | 545 | | | | | |
| TCG | GGC | GGG | TTA | AGC | GTC | GAC | TTT | CTG | GAG | CGG | CCG | GAC | GAG | CTG | CGC | 2071 |
| Ser | Gly | Gly | Leu | Ser | Val | Asp | Phe | Leu | Glu | Arg | Pro | Asp | Glu | Leu | Arg | |
| 550 | | | | | 555 | | | | | 560 | | | | | 565 | |
| GGG | CAG | CTG | ACG | GGA | GAG | AGC | AAG | GCG | GAG | TTG | GAG | CGT | GTT | TGT | CGC | 2119 |
| Gly | Gln | Leu | Thr | Gly | Glu | Ser | Lys | Ala | Glu | Leu | Glu | Arg | Val | Cys | Arg | |
| | | | | | 570 | | | | | 575 | | | | | 580 | |
| GAG | TGG | AAG | GAT | TGG | GAG | GCG | AAG | AGC | CCG | CAT | GGG | AAG | ATC | GAT | TCG | 2167 |
| Glu | Trp | Lys | Asp | Trp | Glu | Ala | Lys | Ser | Pro | His | Gly | Lys | Ile | Asp | Ser | |
| | | | 585 | | | | | 590 | | | | | 595 | | | |
| GGG | TTG | AAG | CAG | CGG | CGA | TGG | GAT | GCG | TGAGGTAGTT | GGGCGGATTG | | | | | | 2214 |
| Gly | Leu | Lys | Gln | Arg | Arg | Trp | Asp | Ala | | | | | | | | |
| | | | 600 | | | | | 605 | | | | | | | | |
| TTTAACACGT | AGTGGGTAAG | GTTGGGGCGG | GTTTGTTTGG | CGTTTTCAGG | GGTTGGGGTG | | | | | | | | | | | 2274 |
| CGGATGCTGG | TCATCCGGGA | AACGGCTCTA | CAACTGGTGT | CAATAGACTA | ATATAGAGTG | | | | | | | | | | | 2334 |

```
ATCAAAGAAC  TGAGGTTCTG  AAAGAGGCGT  GGAAGTCGCG  TTGTGACTCC  CTTTGCCATG      2394

TTGGGAAGTG  TGGCTCAACA  TTGTGTTCAG  GTTTGCTCAG  GGTGATNTCG  AACTGACGTN      2454

TTGATGAGGG  TTATTGCNTA  GA                                                  2476
```

( 2 ) INFORMATION FOR SEQ ID NO: 2:

( i ) SEQUENCE CHARACTERISTICS:
        ( A ) LENGTH: 616 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Scytalidium thermophilum ( x i ) SEQUENCE DESCRIPTION: SEQ ID NO: 2:

```
Met  Lys  Arg  Phe  Phe  Ile  Asn  Ser  Leu  Leu  Leu  Leu  Ala  Gly  Leu  Leu
1              5                        10                       15

Asn  Ser  Gly  Ala  Leu  Ala  Ala  Pro  Ser  Thr  His  Pro  Arg  Ser  Asn  Pro
               20                       25                  30

Asp  Ile  Leu  Leu  Glu  Arg  Asp  Asp  His  Ser  Leu  Thr  Ser  Arg  Gln  Gly
               35                       40                  45

Ser  Cys  His  Ser  Pro  Ser  Asn  Arg  Ala  Cys  Trp  Cys  Ser  Gly  Phe  Asp
     50                            55                  60

Ile  Asn  Thr  Asp  Tyr  Glu  Thr  Lys  Thr  Pro  Asn  Thr  Gly  Val  Val  Arg
65                       70                       75                          80

Arg  Tyr  Thr  Phe  Asp  Ile  Thr  Glu  Val  Asp  Asn  Arg  Pro  Gly  Pro  Asp
               85                       90                       95

Gly  Val  Ile  Lys  Glu  Lys  Leu  Met  Leu  Ile  Asn  Asp  Lys  Leu  Leu  Gly
               100                      105                      110

Pro  Thr  Val  Phe  Ala  Asn  Trp  Gly  Asp  Thr  Ile  Glu  Val  Thr  Val  Asn
               115                      120                      125

Asn  His  Leu  Arg  Thr  Asn  Gly  Thr  Ser  Ile  His  Trp  His  Gly  Leu  His
     130                           135                      140

Gln  Lys  Gly  Thr  Asn  Tyr  His  Asp  Gly  Ala  Asn  Gly  Val  Thr  Glu  Cys
145                           150                      155                 160

Pro  Ile  Pro  Pro  Gly  Gly  Ser  Arg  Val  Tyr  Ser  Phe  Arg  Ala  Arg  Gln
               165                      170                      175

Tyr  Gly  Thr  Ser  Trp  Tyr  His  Ser  His  Phe  Ser  Ala  Gln  Tyr  Gly  Asn
               180                      185                      190

Gly  Val  Ser  Gly  Ala  Ile  Gln  Ile  Asn  Gly  Pro  Ala  Ser  Leu  Pro  Tyr
               195                      200                      205

Asp  Ile  Asp  Leu  Gly  Val  Leu  Pro  Leu  Gln  Asp  Trp  Tyr  Tyr  Lys  Ser
     210                           215                      220

Ala  Asp  Gln  Leu  Val  Ile  Glu  Thr  Leu  Ala  Lys  Gly  Asn  Ala  Pro  Phe
225                           230                      235                 240

Ser  Asp  Asn  Val  Leu  Ile  Asn  Gly  Thr  Ala  Lys  His  Pro  Thr  Thr  Gly
                    245                      250                      255

Glu  Gly  Glu  Tyr  Ala  Ile  Val  Lys  Leu  Thr  Pro  Asp  Lys  Arg  His  Arg
               260                      265                      270

Leu  Arg  Leu  Ile  Asn  Met  Ser  Val  Glu  Asn  His  Phe  Gln  Val  Ser  Leu
               275                      280                      285

Ala  Lys  His  Thr  Met  Thr  Val  Ile  Ala  Ala  Asp  Met  Val  Pro  Val  Asn
               290                      295                      300

Ala  Met  Thr  Val  Asp  Ser  Leu  Phe  Met  Ala  Val  Gly  Gln  Arg  Tyr  Asp
```

```
305                         310                         315                         320
Val Thr Ile Asp Ala Ser Gln Ala Val Gly Asn Tyr Trp Phe Asn Ile
                325                 330                 335

Thr Phe Gly Gly Gln Gln Lys Cys Gly Phe Ser His Asn Pro Ala Pro
            340                 345                 350

Ala Ala Ile Phe Arg Tyr Glu Gly Ala Pro Asp Ala Leu Pro Thr Asp
            355                 360                 365

Pro Gly Ala Ala Pro Lys Asp His Gln Cys Leu Asp Thr Leu Asp Leu
        370             375                 380

Ser Pro Val Val Gln Lys Asn Val Pro Val Asp Gly Phe Val Lys Glu
385                 390                 395                     400

Pro Gly Asn Thr Leu Pro Val Thr Leu His Val Asp Gln Ala Ala Ala
                405                 410                 415

Pro His Val Phe Thr Trp Lys Ile Asn Gly Ser Ala Ala Asp Val Asp
            420                 425                 430

Trp Asp Arg Pro Val Leu Glu Tyr Val Met Asn Asn Asp Leu Ser Ser
        435                 440                 445

Ile Pro Val Lys Asn Asn Ile Val Arg Val Asp Gly Val Asn Glu Trp
    450                 455                 460

Thr Tyr Trp Leu Val Glu Asn Asp Pro Glu Gly Arg Leu Ser Leu Pro
465                 470                 475                 480

His Pro Met His Leu His Gly His Asp Phe Phe Val Leu Gly Arg Ser
            485                 490                 495

Pro Asp Val Ser Pro Asp Ser Glu Thr Arg Phe Val Phe Asp Pro Ala
            500                 505                 510

Val Asp Leu Pro Arg Leu Arg Gly His Asn Pro Val Arg Arg Asp Val
        515                 520                 525

Thr Met Leu Pro Ala Arg Gly Trp Leu Leu Leu Ala Phe Arg Thr Asp
    530                 535                 540

Asn Pro Gly Ala Trp Leu Phe His Cys His Ile Ala Trp His Val Ser
545                 550                 555                 560

Gly Gly Leu Ser Val Asp Phe Leu Glu Arg Pro Asp Glu Leu Arg Gly
                565                 570                 575

Gln Leu Thr Gly Glu Ser Lys Ala Glu Leu Glu Arg Val Cys Arg Glu
            580                 585                 590

Trp Lys Asp Trp Glu Ala Lys Ser Pro His Gly Lys Ile Asp Ser Gly
        595                 600                 605

Leu Lys Gln Arg Arg Trp Asp Ala
    610                 615
```

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGAGACTGAT AACTGGCTTG G           21

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

ACGGCGCATT GTCAGGGAAG T 21

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

Asp Ser Gly Leu Lys
 1                 5

( 2 ) INFORMATION FOR SEQ ID NO:6:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TCGAGATGAA GCGCTTCTTC ATTAATAGCC TTCTGCTTCT CGCAGGGCTC CTCAACTCAG 60

GGGCC 65

( 2 ) INFORMATION FOR SEQ ID NO:7:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

CCTGAGTTGA GGAGCCCTGC GAGAAGCAGA AGGCTATTAA TGAAGAAGCG CTTCATC 57

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GTCATGAACA ATGACCT 17

( 2 ) INFORMATION FOR SEQ ID NO:9:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

AGAGAGTCTA GATTAAACAA TCCGCCCAAC TAC 33